(12) United States Patent
Hazout

(10) Patent No.: US 9,950,040 B2
(45) Date of Patent: Apr. 24, 2018

(54) CELL-FREE DNA AS A THERAPEUTIC TARGET FOR FEMALE INFERTILITY AND DIAGNOSTIC MARKER

(71) Applicant: Ferring B.V., Hoofddorp (NL)

(72) Inventor: Andre Hazout, Paris (FR)

(73) Assignee: FERRING B.V., Hoofddorp (NL)

( * ) Notice: Subject to any disclaimer, the term of this patent is extended or adjusted under 35 U.S.C. 154(b) by 195 days.

(21) Appl. No.: 14/416,835

(22) PCT Filed: Aug. 1, 2013

(86) PCT No.: PCT/IB2013/056321
§ 371 (c)(1),
(2) Date: Jan. 23, 2015

(87) PCT Pub. No.: WO2014/020564
PCT Pub. Date: Feb. 6, 2014

(65) Prior Publication Data
US 2015/0246103 A1  Sep. 3, 2015

(30) Foreign Application Priority Data

Aug. 3, 2012 (EP) .................................... 12179265
Feb. 25, 2013 (EP) .................................... 13156626

(51) Int. Cl.
*A61K 38/46* (2006.01)
*G01N 33/68* (2006.01)
*C12Q 1/68* (2018.01)
*G06F 19/22* (2011.01)

(52) U.S. Cl.
CPC .......... *A61K 38/465* (2013.01); *C12Q 1/6883* (2013.01); *G01N 33/689* (2013.01); *C12Y 301/21001* (2013.01); *G06F 19/22* (2013.01)

(58) Field of Classification Search
CPC ................ A61K 38/465; C12Q 1/6883; C12Y 301/21001; G01N 33/689; G06F 19/22
See application file for complete search history.

(56) References Cited

U.S. PATENT DOCUMENTS

| | | | |
|---|---|---|---|
| 2007/0259367 A1* | 11/2007 | Ax | C12Q 1/34 435/6.16 |
| 2011/0033438 A1* | 2/2011 | Bartoov | A61K 31/00 424/94.6 |
| 2015/0010527 A1* | 1/2015 | Shaaltiel | C12N 9/22 424/94.61 |

FOREIGN PATENT DOCUMENTS

WO    WO 2008/047364 A2    4/2008

OTHER PUBLICATIONS

Yasuda et al. (2002) FEBS Lett. 510(1-2): 22-26.*
Czamanski et al., "Increased plasma cell-free DNA is associated with low pregnancy rates among women undergoing IVF-embryo transfer," Reproductive BioMedicine Online (2013), pp. 36-41.
International Search Report, PCT/IB2013/056321, dated Dec. 2, 2013.
Yasuda et al., "Abrupt pubertal elevation of Dnase I gene expression in human pituitary glands of both sexes," FEBS Letters (2002), pp. 22-26.
Zachariah et al., "Circulating cell-free DNA as a potential biomarker for minimal and mild endometriosis," Reproductive Biomedicine Online (2009), pp. 407-411.

* cited by examiner

*Primary Examiner* — Lisa J Hobbs
(74) *Attorney, Agent, or Firm* — Arrigo, Lee, Guttman & Mouta-Bellum LLP

(57) ABSTRACT

The present invention pertains to the use of DNase to treat female infertility and the use of cfDNA as a marker of female infertility.

10 Claims, 2 Drawing Sheets

Figure 1:
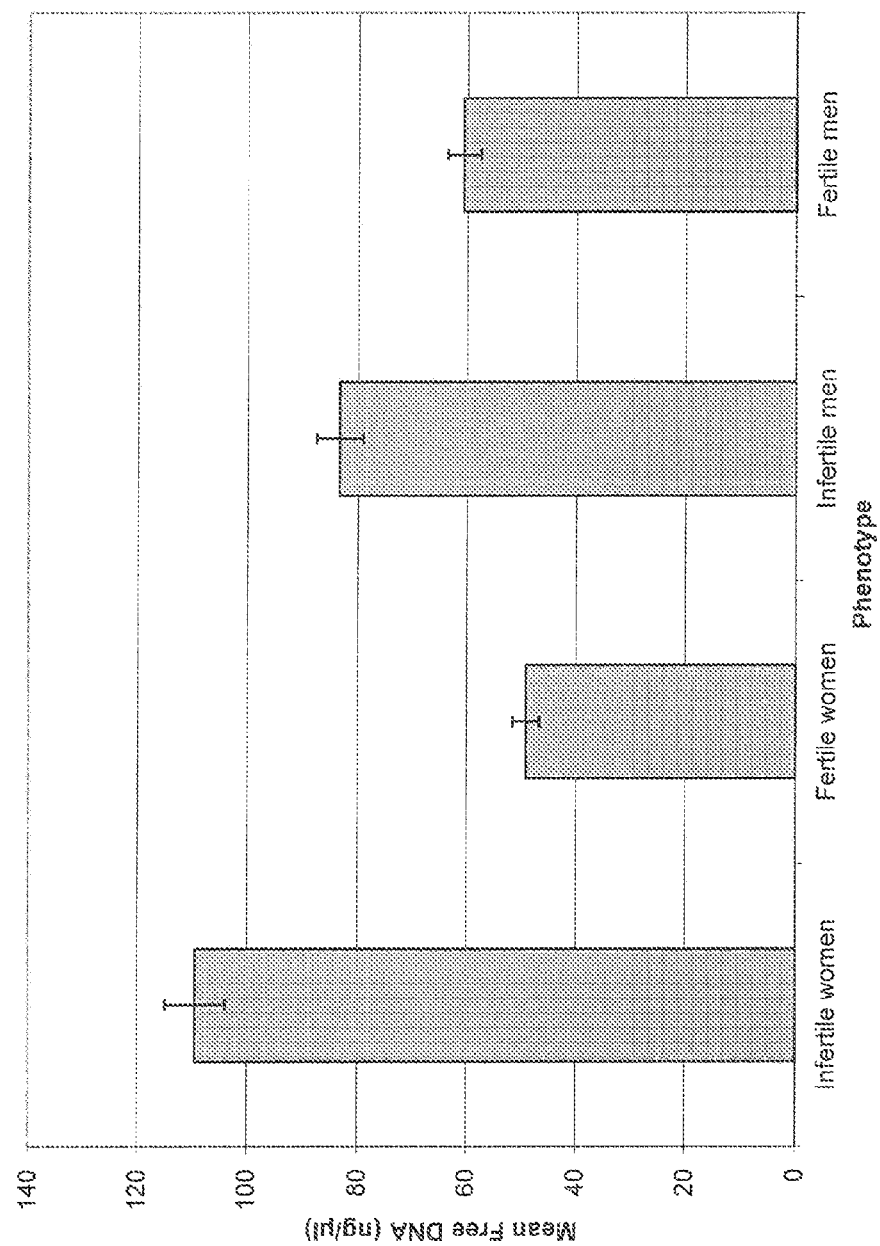

CELL-FREE DNA AS A THERAPEUTIC TARGET FOR FEMALE INFERTILITY AND DIAGNOSTIC MARKER

This is a National Phase Application under 35 U.S.C. § 371 of International Application No. PCT/IB2013/056321, filed Aug. 1, 2013, and claims priority to European Patent Application No. 12179265.9, filed Aug. 3, 2012, and European Patent Application No. 13156626.7, filed Feb. 25, 2013, the content of each of which is incorporated herein by reference.

The instant application contact a Sequence Listing that has been submitted electronically in ASCII format and is hereby incorporated by reference in its entirety. Said ASCII copy, created on May 5, 2015, is named 10192.0064-00000_SL.txt and is 4096 bytes in size.

The present invention relates to the field of female infertility. More precisely, it pertains to a novel marker of female infertility, as well as to a novel treatment to increase the fertility of female patients in need thereof.

In the last few years, authors have reported a prevalence of unexplained infertility as high as 20% to 25%. Infertility is the failure of a couple to conceive a pregnancy after trying to do so for at least one full year.

Diagnosis of infertility begins with the taking of a medical history and physical exam. If the exam is limited to an evaluation of ovulatory function, a hysterosalpingogram and a laparoscopy in any couple not conceiving in one year of attempting, a large number of infertility cases remain unexplained. Expanding the diagnostic tests by adding a number of assays (measurement of the levels of a number of hormones and cytokines, genetic testing techniques to detect any mutation in genes associated, with female infertility) only slightly reduces the "unexplained" infertility.

The deleterious effects of smoking, excess caffeine intake or alcohol use are known. However, their impact on fertility largely differs from one individual to another, and today, no biological marker enables the quantification of this impact. Hence, these effects are not precisely evaluated by currently available tests.

Among treatments for clinical infertility, assisted reproductive technologies (ART) have the highest live birth rate per treatment. ART has contributed to the conception of more than 1 million babies worldwide since its inception. However, the rate of failure of these technologies is still significant and the decision of couples to pursue ART or to repeat ART treatment after a failed attempt is often a difficult decision due to the physical, emotional, and financial costs of treatment.

In vitro fertilization (IVF) and intracytoplasmic sperm injection (ICSI) data clearly indicate, even in the most successful programs, low implantation rates relative to the number of embryos transferred. Defects which lead to problems with implantation are probably much more common than what is currently evaluated and constitute another area of unexplained infertility.

Assaying implantation factors such as integrins, LIF, G-CSF or other growth factors may lead to the understanding of other cases of infertility and hence lower the percentage of patients categorized as having "unexplained infertility", but in most cases this will not assist in the initial deliberations regarding therapy. In France, the ART success rate ranges from 25% to 28% in terms alive birth per oocyte retrieval.

From the above, it appears that a number of parameters involved in female infertility are completely ignored by the current tests.

The presence of circulating cell-free DNA in human plasma was reported in 1948 by Mendel and Metais [1]. Cell-free circulating DNA (cfDNA) has been studied in a wide range of physiological and pathological conditions, including inflammatory disorders, oxidative stress and malignancy. It is present in healthy subjects at blood concentrations ranging from 0 to 100 ng/ml, with an average of 30 ng/ml [2]. Assuming that the DNA content of a normal cell amounts to 6.6 pg, these values represent an average of 0-15,000 genome equivalents per ml of blood, with an average of 5000 genomes per ml. Most of this DNA is double-stranded and is apparently in the form of nucleoprotein complex.

Electrophoresis of cfDNA on low-percentage agarose gels has shown a variation in the size of DNA fragments of between 0.18 and 21 kilobases, with variations from sample to sample in the size distribution of DNA fragments. It is common to detect large, quasi-genome size DNA fragments.

Although the precise mechanism associated with the release of free DNA into the bloodstream remains uncertain, it probably derives from a combination of apoptosis, necrosis and active release from cells.

The clearance of cfDNA from the bloodstream occurs rapidly: fetal DNA disappeares from the blood of mothers after delivery with a half-life of 16.3 minutes [3]. It is known that cfDNA is sensitive to plasma nucleases (e.g., DNase I), but renal [4] and hepatic [5] clearance mechanisms are also involved in the elimination of cfDNA.

So far, it is unknown if the release of cfDNA has any biological effects. Cultured cells have been shown to release double stranded DNA into the media [6], and cfDNA might be incorporated into cells [7]. These findings led to the introduction of the concept of "genometastasis" [8]. However, this hypothesis remains to be proven.

Circulating DNA can be isolated from both plasma and serum, but serum contains approximately 6-times higher concentration of circulating DNA. Recently, Umetani et al. showed that less than 10% of the 6-fold higher serum DNA levels were due to contamination by other sources (i.e., release from leucocytes during the separation of serum) [9]. The reason for higher serum levels remains unknown, but a loss of DNA in plasma during purification procedures was excluded [9].

Cell-free circulating DNA is a potentially useful biomarker. DNA levels and fragmentation patterns offer interesting possibilities for diagnostic and prognostic purposes. Recently, Bartoov et al. described a method for assessing the fertility status of a male subject, based on the measurement of cfDNA in a fluid sample from said subject (WO2008/047364). They also proposed a method for treating male sub-fertility by administering DNase to sub-fertile males. Cell-free DNA was also proposed as a biomarker for non-invasive monitoring of malignant and benign proliferations and inflammatory conditions, such as endometriosis [10].

Very recently, Czamanski-Cohen et al. reported that in a cohort of 37 women undergoing IVF treatment, plasma cfDNA concentrations were statistically higher on the day of βHCg test in women who did not conceive, in comparison to those who conceived. However, as recognized by the authors, this study could not establish a correlation between female infertility and cfDNA concentration, since all the women included therein were in the process of IVF treatment [11].

As described herein, the inventor has now demonstrated that the cfDNA level is statistically higher in infertile women than in fertile ones. Hence, the level of cfDNA can be useful for the diagnosis and prognosis of infertility. The level of cfDNA can also be useful for the diagnosis and prognosis of infertility in women not suffering from endometriosis. The fact that cfDNA can be obtained without invasive or painful procedures makes it particularly suitable for use in diagnosis of infertility in women. Moreover, as demonstrated in the experimental part below, a treatment leading to a decrease of cell-free DNA level significantly improves the fertility of the treated female patients.

A first aspect of the present invention is hence a method for in vitro diagnosing infertility in a mammalian female, comprising the following steps:
(i) determining the level of cell-free DNA in a body fluid sample from said female, and
(ii) comparing said level to a predetermined threshold, wherein a level of cell-free DNA above said predetermined threshold is indicative of infertility.

This method can be used to diagnose infertility in a human or animal female, preferably in human. It can be performed either together with the first tests which are done when the reasons for infertility of a couple are explored, or after these tests, in patients for which the tests failed to identify a cause of infertility. In particular, it can be used for in vitro diagnosing infertility in a female not suffering from endometriosis.

Of course, in what precedes, a female who has a cfDNA level "indicative of infertility" means that this female has a probability of being infertile which is higher than that of a female who has a cfDNA below the predetermined threshold.

In the above method, the body fluid sample can be a sample of plasma, serum, blood or follicular fluid.

As shown in the experimental part below, cfDNA concentration was measured in the plasma of 94 fertile women and 96 infertile women. In this cohort, the average cfDNA plasmatic concentration was around 50 ng/µl in fertile women and around 109 ng/µl in infertile ones. Hence, when the above method concerns human females and when the body fluid sample is a plasma sample, the threshold will be chosen between the two values, and preferably between about 50 and about 100 ng/µl. Of course, the skilled worker will be able to refine and modify these values by further investigating this parameter on a larger cohort of patients. By measuring the cfDNA level in samples from a larger amount of patients, the skilled in the art will also establish a scale of values for the cfDNA level, with corresponding probabilities of infertility. Measurements in larger cohorts, comprising homogeneous sub-groups of women (depending on their age and/or behavior parameters such as whether they smoke or not and/or physiological parameters such as weight, HbAlc and the like) may also lead to the determination of different thresholds reflecting the different situations. In this case, the skilled in the art will determine the probability of infertility of a woman by interpreting her cfDNA level in view of the other relevant parameters.

As already mentioned, the method can be performed by measuring the cfDNA level in a body fluid sample different from plasma sample. Of course, for each body fluid, measurements have to be performed in a significant cohort of females, including fertile and infertile ones, to determine a relevant threshold.

The threshold will be chosen close to the average value of fertile females if the aim is to identify all or nearly all the females who may be infertile. In this case, fertile females may also be diagnosed as likely to be infertile (false positive). To the contrary, if the aim is to identify only those who have the highest probability of being infertile, the threshold will be chosen close to the average value of infertile females.

In one specific embodiment, the method according to the invention is performed for in vitro diagnosing infertility in a woman by measuring the level of cfDNA in a plasma sample from said woman, and a plasma level of cfDNA above 60 ng/µl is indicative of infertility.

In another embodiment, the method according to the invention is performed for in vitro diagnosing infertility in a woman by measuring the level of cfDNA in a plasma sample from said woman, and a plasma level of cfDNA above 70 ng/µl is indicative of infertility.

In another embodiment, the method according to the invention is performed for in vitro diagnosing infertility in a woman by measuring the level of cfDNA in a plasma sample from said woman, and a plasma level of cfDNA above 80 ng/µl is indicative of infertility, wherein a level of cell-free DNA above said predetermined threshold is indicative of infertility.

In another embodiment, the method according to the invention is performed for in vitro diagnosing infertility in a woman by measuring the level of cfDNA in a plasma sample from said woman, and a plasma level of cfDNA above 90 ng/µl is indicative of infertility, wherein a level of cell-free DNA above said predetermined threshold is indicative of infertility.

In yet another embodiment, the method according to the invention is performed for in vitro diagnosing infertility in a woman by measuring the level of cfDNA in a plasma sample from said woman, and a plasma level of cfDNA above 100 ng/µl is indicative of infertility.

According to another aspect, the present invention pertains to a kit for performing the above methods. In particular, the invent on is directed to a kit comprising reactants for measuring the level of cfDNA in a biological sample, and reactants specific for measuring at least one other physiological parameter in a biological sample, wherein said physiological parameter is selected from the group consisting of the level of anti-müllerian hormone (AMH), telomerase activity and homocysteine concentration.

The level of cfDNA in a biological sample can be measured by any technique known in the art, such as but not limited to any nucleic acid stain, such as for example, intercalators. Non-limitative examples of DNA intercalators which can be used to measure cfDNA levels and included in the kits according to the present invention include berberine, ethidium bromide, proflavine, daunomycin, doxorubicin, thalidomide, Sybr® Green, Sybr® Gold and PicoGreen®.

Anti-Mullerian Hormone (AMH) is also called MIS (Mullerian Inhibiting Substance). Since AMH is produced directly by the ovarian follicles, AMH levels correlate with the number of antral follicles in the ovaries. It has been documented that women with lower AMH have lower antral follicular counts and produce a lower number of oocytes compared with women with higher levels. AMH blood levels are thought to reflect the size of the remaining egg supply—or "ovarian reserve". AMH can be measured by immune-assay such as ELISA. A kit according to the invention can hence comprise an anti-AMH antibody.

Telomerase is an enzyme which repairs DNA degradation. However, it can be ineffective if present in insufficient concentration. Besides, when present in too high a concentration, telomerase generates apoptotic factors. As a consequence, telomerase is also implicated in fertility and impacts on early embryonic development. Its level can be measured by immunoassay, and hence, a kit according to the present invention can comprise an antibody specifically recognizing telomerase.

Homocysteine is a non-protein homologue of the amino acid cysteine, differing by an additional methylene (—CH2-) group. It is a marker of oxidative stress, and as such, can be informative about the fertility status of an individual. Homocysteine levels can be measured by enzymatic assays: bound or dimerised homocysteine (oxidised form) is reduced to free homocysteine, which then reacts with serine catalysed by cystathionine beta-synthase (CBS) to form L-cystathionine. Cystathionine in turn is broken down by cystathionine beta-lyase (CBL) to form homocysteine, pyruvate and ammonia. Pyruvate is then converted by lactate dehydrogenase (LDH) to lactate with NADH as coenzyme. The rate of NADH conversion to NAD is directly proportional to the concentration of homocysteine (ΔA340 nm).

According to a particular embodiment, the kit according to the present invention comprises at least one DNA intercalating agent and an antibody specifically recognizing AMH.

As described in the experiments below, infertile women who had already undertaken several treatments including several IVF without success, were treated with a deoxyribonuclease. After only one round of treatment with the deoxyribonuclease, followed by ART, more than 50% of these patients became pregnant. Hence, the present invention also pertains to a deoxyribonuclease, for use in the treatment of female infertility, especially when this infertility is associated with a level of cell-free DNA higher than the level of cell-free DNA which is statistically observed in fertile women.

Deoxyribonuclease (DNase) is an enzyme that catalyzes the hydrolytic cleavage of phosphodiester linkages in DNA backbone. The deoxyribonucleases are thus a type of nuclease. A wide variety of deoxyribonucleases are known, which differ in their substrate specificities, chemical mechanisms and biological functions.

Sonic DNases cleave only residues at the ends of DNA molecules (exodeoxyribonucleases, a type of exonuclease). Others cleave anywhere along the chain (endodeoxyribonucleases, a subset of ribonucleases). Some are very sequence-specific about the DNA sequence at which they cut, like restriction enzymes, while others are fairly indiscriminate. Some cleave only double-stranded DNA, others are specific for single-stranded molecules, and others act on both.

Deoxyribonuclease I cleaves DNA preferentially at phosphodiester linkages adjacent to a pyrimidine nucleotide, yielding 5'5'-phosphate-terminated polynucleotides with a free hydroxyl group on position 3', on average producing tetranucleotides. It acts on single-stranded DNA, dsDNA, and chromatin.

Deoxyribonuclease II (Acid DNase) hydrolyzes deoxyribonucleotide linkages in native and denatured DNA yielding products with 3'-phosphates. As the name suggests, it is more efficient in acidic pH. There are several known DNase II, including the alpha DNase II (usually just called DNase II) and DNase II beta (also called DLAD or DNase II-Like Acid DNase).

Although any type of DNase can be used in the present invention, DNase I is preferred. Recombinant human DNase I is already clinically used. DNase enzymes can be inhaled using a nebulizer by cystic fibrosis sufferers. DNase enzymes help because white blood cells which accumulate in the mucus break down and release DNA, which adds to the 'stickiness' of the mucus. DNase breaks down the DNA and the mucus is easier to clear from the lungs.

The present invention also pertains to a method for treating female infertility. In a specific embodiment, the present invention pertains to a method for treating female infertility in a female who does not suffer from endometriosis. In another specific embodiment, the present invention pertains to a method for treating female infertility in a female exhibiting a level of cell-free DNA higher than that statistically observed in fertile female. In any of its embodiments, the method according to the invention comprises administering a deoxyribonuclease to a female in an amount which is sufficient to decrease her cell-free DNA level to a level similar to that observed in fertile female. In what precedes, the "level of cell-free DNA" is to be understood as the concentration of cell-free DNA in any relevant body fluid, such as plasma, serum, blood, or follicular fluid. In what follows, infertile females having a high level of cfDNA (compared to fertile females) will be designated as being "in need of" a treatment as herein disclosed. The present invention is particularly advantageous for treating infertility in women.

In the present invention, a recombinant human DNase can advantageously be used, especially for treating women. Of course, when a female from another species is treated, a recombinant DNase from this species is preferred. As already mentioned, any DNase can be used to perform this invention, but DNase I is preferred.

When performing the present invention, any administration route can be used, provided it leads to the delivery of a sufficient amount of DNase to obtain a decrease of circulating cell-free DNA. For example, the DNase can be administered by intravenous or intramuscular route.

For the treatment of infertility, the DNase will be administered in an amount sufficient to obtain a decrease in the level of cell-free DNA in blood and/or in the follicular fluid. For example, a minimum 2500 UI of DNase I can be administered each day to an infertile female, during at least 2 days, preferably at least 3 or 4 days or more. Of course, due to inter-individual diversity, different responses can be observed, and the dosage regimen can be adapted in consequence, so that the dose which is administered is sufficient to obtain a decrease of the cell-free DNA level, which must become similar to the levels observed in fertile patients. The cfDNA level can be followed-up to check its decrease and avoid unnecessary treatment.

It has been observed that after the decrease of cfDNA level and after the treatment is stopped, the cfDNA level does not increase quickly to reach its former values. During at least a few days, the cfDNA level stays approximately stable. As a consequence, the DNase can advantageously be administered to an infertile female in need thereof during the late luteal phase.

According to a particular embodiment of the invention, illustrated in the experimental part below, 2500 UI of DNase I are administered twice a day to an infertile female in need thereof, during 7 days of the late luteal phase.

Of course, the above-described method of treatment of infertility can be combined with ART, as described in the experiments hereafter.

The invention is further illustrated by the following figures and examples.

LEGENDS TO THE FIGURES

FIG. 1: Mean cfDNA concentrations in blood plasma of 73 fertile and 88 infertile men and in 94 fertile and 96 infertile women.

Figure 2:
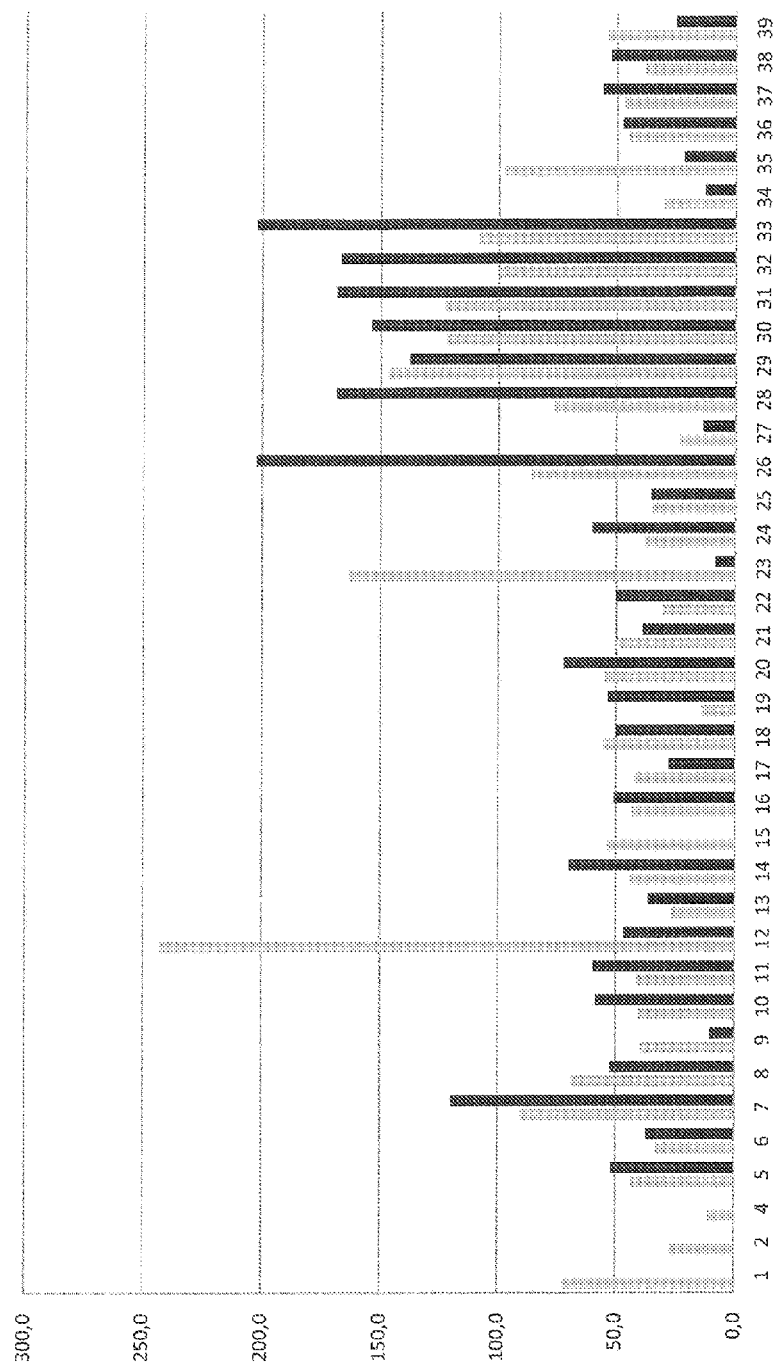

FIG. 2: CfDNA concentrations in blood plasma (black boxes) and in follicular fluid (grey boxes) from 37 women. Those women of this group who became pregnant had a mean cfDNA level in plasma and/or in follicular fluid which was lower than the mean value for all the women of the group (including those who became pregnant and those who did not).

EXAMPLES

Example 1: Patients, Materials and Methods

Semen Samples

Semen samples from fertile and infertile men aged <50 were collected by masturbation after 3-6 days of sexual abstinence. Sperm counts and motility, vitality, and morphology analysis were performed according to the World Health Organization guidelines. A total of 161 men were included in this study: 73 fertile men and 88 infertile.

Plasma and Follicular Fluid Samples from Females

Cell-free DNA (cfDNA) quantity in plasma has been measured in 94 fertile (AMH>2 ng/ml) and in 96 infertile women aged less than 37 years. A genomic study was carried out to verify the origin of this cfDNA, particularly in infertile women.

When samples were available, cfDNA quantification was also performed in follicular fluid samples in corresponding infertile women. A total of 37 follicular fluid samples were included in this study.

Ovarian Stimulation and Follicular Fluid Retrieval

Most patients were stimulated for ART using a long agonist protocol or antagonist protocols with recombinant FSH (Gonal F® (Merck laboratory) or Puregon® (Schering Plough laboratory)) or HMG (Menopure®: Ferring laboratory)). After hormonal and sonographic controls, the ovulation was triggered with recombinant or urinary HCG, 36 hours before oocyte retrieval according to a well known technique. Two or three dominant follicular fluids were isolated and centrifuged before storage. Then cfDNA content was evaluated using the same method as in plasma/serum.

CfDNA Isolation and PCR Amplification

Plasma cfDNA was isolated using a High Pure PCR template preparation kit (Roche) following manufacturer's recommendation. Elution buffer was diluted to a 20% solution by using dd$H_2O$ and prewarmed at 70° C. Samples were centrifuged at 16,000 g for 5 min, 400 µl of plasma were transferred to a 2 ml Eppendorf tube avoiding cellular debris. 400 µl of binding buffer and 40 µl of reconstituted proteinase K were mixed to the samples. After a brief vortex, the tubes were incubated 10 min at 70° C. After incubation 200 µl of 100% isopropanol were mixed to the samples that were consequently transferred to the upper reservoir of a high pure filter collection tube provided in the High Pure PCR template preparation kit. The column was centrifuged at 8,000 g for 1 mm at room temperature. The flow-through and collection tubes were discarded and the filter was combined to a new collection tube. This loading step was repeated until the entire sample had been loaded to the filter. 500 µl of inhibitor removal buffer were added to the upper reservoir and centrifuged 1 min at 8,000 g at room temperature. The flow-through and collection tubes were discarded and the filter was combined with a new collection tube. The tubes were washed twice by adding 500 µl of wash buffer to the upper reservoir and centrifuged 1 min at room temperature. Columns were dried by centrifuging at maximum speed (approximately 13,000 g) for 10 s, transferred to a new 1.5-ml Eppendorf tube and warmed 5 min at 70° C. in an incubator. 100 µl of pre-warmed 20% elution buffer were carefully added to the filter. The tube and filter were placed in the incubator at 70° C. and shook at low speed (approximately 400 rpm) for 5 min. DNA samples were eluted from the columns by centrifuging at 8,000 g for 5 min and subsequently stored at 4° C. before use or frozen at −70° C. for long term storage.

PCR Amplification

The master mix used to amplify the JmJC2 and DXS1285 loci contained 200 mM of each dNTP, 1×Taq polymerase buffer, 2 µM of each primer sets, 1.5 mM MgCl2, and 0.5 U of Biotaq™ DNA polymerase (Bioline) in a 15 µl reaction volume. The sequences of primers used to amplify JmJC2 (marker of Y chromosome) and DXS1285 (marker of X chromosome) are

```
                                      (SEQ ID No: 1)
    5'-GAGTATGCGACCAGT-3', (SEQ ID No: 2)
    5'-TGGCACACCATGGGA-3'
    and (SEQ ID No: 3)
    5'-CGTGCTTAGGCTTAATCCC-3', (SEQ ID No: 4)
    5'-GAACTGACTGTAGAGAAGG-3',
``` respectively, with a 60° C. annealing.

cfDNA Quantification

Blood samples were collected in EDTA-containing vacutainer tubes. They were centrifuged (3,400 rpm for 15 minutes) for plasma isolation. Before cfDNA quantification, plasma and follicular fluid sample were centrifuged at 3,400 g for 20 min. Samples have to be transparent with no red blood cells. Indeed cfDNA quantification can be altered in coloured samples. Standard DNA solution was diluted to 20, 50, 100 and 500 ng/ml in 166 µl to draw the standard curve. 166 µl of 1N $HCLO_4$ (perchloric acid) and 664 µl of diphenylamine were added to each 166 µl of plasma or follicular fluid supernatant samples. Samples Were incubated at 37° C. for 20 h, subsequently centrifuged at 15,000 g for 10 minutes. 300 µl of the supernatant were transferred to a 96-well plate and measured in spectrophotometer (Tecan, Genios) at 600 nm.

DNase Treatment

The patients were enrolled after obtaining their written informed consent.

In the late luteal phase of a preceding cycle, 10 selected women with very high levels of cfDNA (>100 ng/microliter) were treated with one ampoule of Dornase alpha (Pulmozyme®) 2.5 mg (2500 IU), twice a day, via intramuscular route, for seven days.

Pulmozyme® (dornase alfa) Inhalation Solution is a sterile, clear, colorless, highly purified solution of recombinant human deoxyribonuclease I (rhDNase) which selectively cleaves DNA.

Pulmozyme® is normally administered by inhalation of an aerosol mist produced by a compressed air driven nebulizer system. But the systemic levels of rhDNase was very low (maximum 15%) after inhalation, so it was decided to order this same product for IM injection to increase the DNase concentration, assuming the fact that there was no side effect in the toxicologic study of Pulmozyme, even by intravenous way.

Statistics

A bilateral t-test was used to evaluate differences in cfDNA levels between fertile and infertile individuals. Correlation coefficients were calculated using Spearman correlation two-sided test. Statistical differences were considered significant when P<0.05.

Example 2: cfDNA and Male Infertility

The aim of this first preliminary study was to verify the concept of an association between male infertility and high levels of cfDNA, assuming the fact that DNA fragmentation may participate to increased cfDNA.

In order to evaluate the integrity of cfDNA, PCR were performed on isolated cfDNA samples. An X chromosome marker was amplified with cfDNA isolated from plasma of both men and women. A Y chromosome marker was amplified with cfDNA isolated from male plasma but not from female plasma.

Higher levels of cfDNA were detected in blood plasma samples from infertile individuals as compared to respective fertile controls. cfDNA quantity in plasma has been measured in 73 fertile (60.7 ng/µl±46.9) and 88 infertile men (83.3 ng/µl±64.8), p=8.7e-3 (FIG. 1).

Example 3: cfDNA in Blood Plasma from Women

As in men, higher levels of cfDNA were detected in blood plasma samples from infertile women as compared to respective fertile controls. The difference between fertile and infertile individuals was however greater in women than in men.

Indeed, cfDNA quantity in plasma of 94 fertile women proved to be two-fold lower (49.2 ng/µl±58.0) than in 96 infertile women (109.4 ng/µl±88.1), p=1.02e$^{-7}$ (FIG. 1).

Example 4: CfDNA Quantity in Blood Plasma vs Follicular Fluid in 37 Infertile Women The cfDNA concentration in blood plasma was compared to that in follicular fluid. A statistically significant positive correlation was found between blood plasma cfDNA concentration and follicular fluid (r=0.43, p=6.4e$^{-3}$) (FIG. 3). In a preliminary study, pregnant women had less cfDNA in follicular fluid and serum than non pregnant women (data not shown).

Example 5: Effects of DNase Treatment on Blood Plasma cfDNA Concentration and Fertility To this day, 10 patients who have been infertile for more than four years and/or had an history of several IVF/ICSI failures without any explanation, were treated for seven days in the late luteal phase of a previous cycle immediately before ovulation induction treatment starting at the second day of the next cycle and using recombinant or urinary FSH with GnRH agonist or antagonist. All patients obtained cleaved embryos and one or several embryos at day 3 were transferred per patient.

For each patient, a blood sample as collected immediately before and after the DNase I treatment to quantify cfDNA in the plasma.

Six of these patients became pregnant after only one such treatment, giving birth to seven children (one abortion, 4 single births and 1 triple birth). The data relative to the treated patients are shown in tables 1 and 2 below:

TABLE 1 age and infertility history of the included patients

| Patient | Age | Infertility history |
|---|---|---|
| # 1 | 28 | 5 ART failures |
| # 2 | 33 | 8 ART failures |
| # 3 | 32 | 4 ART failures |
| # 4 | 35 | 6 Art failures |
| # 5 | 37 | 4 ART failures |
| # 6 | 40 | 4 ART failures |
| # 7 | 34 | 2 ART failures |
| # 8 | 24 | 4 ART failures |
| # 9 | 37 | 2 ART failures; 10 years of unexplained infertility; one miscarriage after ICSI |
| # 10 | 37 | 2 ART failures |

TABLE 2 cfDNA concentrations immediately before and after treatment and outcome

| Patient | cfDNA before treatment (ng/µL) | cfDNA after treatment (ng/µL) | Outcome |
|---|---|---|---|
| # 1 | 103.3 | 65.2 | Gave birth to a single child |
| # 2 | 91.0 | 61.8 | Gave birth to a single child |
| # 3 | 161.2 | 140.7 | Gave birth to triplets |
| # 4 | 110.0 | 78.3 | No pregnancy |
| # 5 | 116.1 | 56.0 | Gave birth to a single child |
| # 6 | 153.5 | 124.9 | No pregnancy |
| # 7 | 160.7 | 138.7 | No pregnancy |
| # 8 | 151.8 | 92.2 | Gave birth to a single child |
| # 9 | 127.9 | 85.2 | TESE (Biochemical pregnancy) |
| # 10 | 87.8 | 77.2 | No pregnancy |

As appears in Table 2, all patients who became pregnant had a decrease of cfDNA after DNase I therapy. The only abortion was considered to be due to the bad quality of testicular sperm. In certain patients who did not become pregnant, the fall of cfDNA was moderate, suggesting that the dose of DNase I should be increased in certain cases with very high levels of cfDNA.

Discussion

The short preventive treatment of women from infertile couples prior to IVF/ICSI, according to their free DNA levels, with DNase led to pregnancy in more than 50% of cases. All the treated women showed more than 4 years of unexplained infertility or many embryo transfers, at early stage of development, without implantation.

REFERENCES

1—Mandel P. Metais P. Les acides nucleiques du plasma sanguine chez l'homme. C R Acad Sci Paris 1948; 142: 241-3.

2—Huang Z H, Li L H, Hua D. Quantitative analysis of plasma circulating DNA at diagnosis and during follow-up of breast cancer patients. Cancer Lett 2006; 243: 64-70.

3—Lo Y M, Zhang J, Leung T N, et al. Rapid clearance of fetal DNA from maternal plasma. Am J Hum Genet 1999; 64: 218-24.

4—Botezatu I, Serdyuk O, Potapova G, et al. Genetic analysis of DNA excreted in urine: a new approach for detecting specific genomic DNA sequences from cells dying in an organism. Clin Chem 2000: 46: 1078-84.

5—Minchin R F, Carpenter D, Orr R J. Polyinosinic acid and polycationic liposomes attenuate the hepatic clearance of circulating plasmid DNA. J Pharmacol Exp Ther 2001; 296: 1006-12.

6—Anker P, Stroun M, Maurice P A. Spontaneous release of DNA by human blood lymphocytes as shown in an in vitro system. Cancer Res 1975; 35: 2375-82.

7—Bergsmedh A, Szeles A, Henriksson M, et al, Horizontal transfer of oncogenes by uptake of apoptotic bodies. Proc Natl Acad Sci USA 2001; 98: 6407-11.

8—Garcia-Olmo D C, Ruiz-Piqueras R, Garcia-Olmo D. Circulating nucleic acids in plasma and serum (CNAPS) and its relation to stem cells and cancer metastasis: state of the issue. Histol Histopathol 2004; 19: 575-83.

9—Umetani N, Hiramatsu S, Hoon D S. Higher amount of free circulating DNA in serum than in plasma is not mainly caused by contaminated extraneous DNA during separation. Ann N Y Acad Sci 2006; 1075: 299-307.

10—Zachariah R, Schmid S, Radpour R, Buerki N, Fan A X, Hahn S, Holzgreve W, Zhong X Y. Circulating cell-free DNA as a potential biomarker for minimal and mild endometriosis. Reprod Biomed Online. 2009 March; 18(3):407-11.

11—Czamanski-Cohen J, Sarid O, Cwikel J, Lunenfeld F, Douvdevani A, Levitas E, Har-Vardi I. Increased plasma cell-free DNA is associated with low pregnancy rates among women undergoing IVF-embryo transfer. Reprod Biomed 2013 January; 26(1):36-41.

The invention claimed is:

1. A method for improving female fertility in a female patient in need thereof comprising:
   administering at least 2500 UI of DNase for at least two days to a female patient having a plasma level of cell-free DNA above 60 ng/μl.

2. The method according to claim 1, wherein the female patient has a plasma level of cell-free DNA above 80 ng/μl.

3. The method according to claim 1, wherein the patient does not have endometriosis.

4. The method according to claim 1, wherein the DNase is a recombinant DNase.

5. The method according to claim 1, wherein the DNase is DNase I.

6. The method according to claim 1, wherein the DNase is administered by intravenous or intramuscular route.

7. The method according to claim 1, wherein the DNase is administered to the patient during the late luteal phase.

8. The method according to claim 1, wherein the patient is a human female.

9. The method according to claim 1, wherein the effective amount of DNase comprises 2500 UI of DNase I administered each day to the patient, for at least 4 days.

10. The method according to claim 1, wherein the effective amount of DNase comprises about 2500 UI of DNase I administered twice a day to the patient, for 7 days of the late luteal phase.

\* \* \* \* \*

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Synthetic Primer

<400> SEQUENCE: 1
gagtatgcga ccagt                                                    15

<210> SEQ ID NO 2
<211> LENGTH: 15
<212> TYPE: DNA
<213> ORGANISM: Artificial Sequence
<220> FEATURE:
<223> OTHER INFORMATION: Synthetic Primer

<400> SEQUENCE: 2
tggcacacca tggga                                                    15

<210> SEQ ID NO 3
<211> LENGTH: 19
<212> TYPE: DNA
<213> ORGANISM: Artificial Sequence
<220> FEATURE:
<223> OTHER INFORMATION: Synthetic Primer

<400> SEQUENCE: 3
cgtgcttagg cttaatccc                                                19

<210> SEQ ID NO 4
<211> LENGTH: 19
<212> TYPE: DNA
<213> ORGANISM: Artificial Sequence
<220> FEATURE:
<223> OTHER INFORMATION: Synthetic Primer

<400> SEQUENCE: 4
gaactgactg tagagaagg                                                19
```